United States Patent [19]
Elias et al.

[11] Patent Number: 6,071,955
[45] Date of Patent: Jun. 6, 2000

[54] FXR, PPARA AND LXRA ACTIVATORS TO TREAT ACNE/ACNEIFORM CONDITIONS

[75] Inventors: Peter M. Elias; Karen Hanley, both of Mill Valley; Kenneth R. Feingold, San Rafael, all of Calif.

[73] Assignee: The Regents of the University of California, Oakland, Calif.

[21] Appl. No.: 09/257,356

[22] Filed: Feb. 25, 1999

[51] Int. Cl.[7] .................................................. A61K 31/335
[52] U.S. Cl. .............................................................. 514/475
[58] Field of Search ..................... 514/167, 675, 514/355, 171, 544, 475; 424/59

[56] References Cited

U.S. PATENT DOCUMENTS

| | | |
|---|---|---|
| 4,871,752 | 10/1989 | L. Ilg et al. . |
| 5,161,481 | 11/1992 | Laufer ...................... 119/205 |
| 5,556,844 | 9/1996 | Reichert et al. . |
| 5,587,367 | 12/1996 | Reichert et al. . |
| 5,604,262 | 2/1997 | Wood ....................... 514/675 |
| 5,837,224 | 11/1998 | Voorhees et al. .......... 424/59 |

FOREIGN PATENT DOCUMENTS

| | | | |
|---|---|---|---|
| 0465343B1 | 6/1994 | European Pat. Off. . | |
| 870498 | 10/1998 | European Pat. Off. ......... | A61K 9/70 |
| 2323783 | 7/1998 | United Kingdom ......... | A61K 31/495 |
| 9621742 | 7/1996 | WIPO ............................... | C12Q 1/68 |
| 9832444 | 7/1998 | WIPO ............................ | A64K 31/56 |

OTHER PUBLICATIONS

Weinberger C., A Model For Farnesoid . . . , Trends In Endo,. And Metab, vol. 7/1, pp. 1–6 (Jan. /1996).

Noonan et al., A hypothetical mechanism . . . , Adv. Exp. Med. Biol., vol. 422, pp. 127–135 (1997).

Hanley et al., Activators of the nuclear . . . , J. Clin. Invest., vol. 100/3, pp. 705–712 (1997).

Kubo et al., Naturally occurring antiacne agents, J. Of Natural Products, vol. 57/1, pp. 9–17, (1994).

M. Duffill et al. (1976) *British Journal of Dermatology* 94: 355–362.

J.T. Elder et al. (Feb. 1994) *Arch Dermatol* 130: 216–224.

L. Skov et al. (Feb. 1997) *American Journal of Pathology* 150(2): 675–683.

G.D. Weinstein et al. (1965) *the Journal of Investigative Dermatology* 50(3): 254–259.

*Primary Examiner*—William R. Jarvis
*Assistant Examiner*—Vickie Kim
*Attorney, Agent, or Firm*—Townsend and Townsend and Crew LLP

[57] ABSTRACT

Acne *vulgaris* and acneiform skin conditions are treated by the application of compounds that is juvenile hormone III, 7-methyl-9-(3,3-dimethyloxiranyl)-3-methyl-2,6-nonadienoic acid methyl ester.

3 Claims, No Drawings

# FXR, PPARA AND LXRA ACTIVATORS TO TREAT ACNE/ACNEIFORM CONDITIONS

GOVERNMENT RIGHTS

This invention was made at least in part with assistance from the United States Federal Government, under Grant No. HD 29706 of the National Institutes of Health. As a result, the Government has certain rights in this invention.

This invention resides in the technical field of therapeutic agents for the treatment of acne *vulgaris* and acneiform skin conditions.

BACKGROUND OF THE INVENTION

Acne *vulgaris* is a chronic skin condition characterized mainly by comedones and papules. In severe cases, inflammation, pustules, cysts a scarring may occur. Acne occurs most often in adolescence, but may also occur in prepubertal children and in older persons. Acne *vulgaris* has its origin in the pilosebaceous units in the dermis, i.e., the hair follicles and associated sebaceous glands. Acne generally arises from an increase in androgen levels arising from an increasing influx in circulatory testosterone. This in turn causes the sebaceous glands to increase in size and activity, producing larger amounts of sebum and increased keratinization of the follicular walls, which blocks the sebum flow, dilating the follicle and entrapping sebum and cellular debris.

Control of acne is achieved by a combination of personal hygiene (including skin cleansing and dietary control) and the use of therapeutic agents. A prominent component of a regiment for controlling acne is the removal of excess sebum from the skin by thorough daily washing and the avoidance of topically applied fats and oils.

Therapeutic agents for acne and acneiform conditions are classified in three groups—(a) systemic and topical antibiotics, (b) peeling agents, and (c) retinoids. Systemic and topical antibiotics include tetracycline, erythromycin, minocycline, and clindamycin, but use of these agents is often accompanied by drug side effects, the development of resistance, and changes in the normal microbial flora. Peeling agents include benzoyl peroxide and salicylic acid, which unfortunately at times act as irritants or mutagens, particularly when combined with sun exposure. Retinoids include tretinoin (vitamin A or retinoic acid), which is applied topically to inhibit follicular keratinization, and isotretinoin (13-cis-retinoic acid), which is applied systemically to suppress sebaceous glands. Retinoids are often irritants and are not advised for individuals with sensitive skin. Retinoids can also be phototoxic, and they can induce thin and easily bruisable, fragile skin.

SUMMARY OF THE INVENTION

It has now been discovered that the acne and acneiform skin conditions can be treated and controlled by the administration of certain activators of any one of three nuclear receptors—the farnesoid X-activated receptor (FXR), the peroxisome proliferator-activated receptor $\alpha$ (PPAR$\alpha$), and the liver-based receptor known as LXR$\alpha$. These three receptors are nuclear receptors and are part of the nuclear receptor superfamily of transcription factors. The three receptors reside in a subgroup of the superfamily, all receptors in the subgroup sharing the feature, with the retinoid receptor RAR, that they function only when having formed heterodimers with the retinoid X receptor (RXR).

DETAILED DESCRIPTION OF THE INVENTION AND PREFERRED EMBODIMENTS

The farnesoid X-activated receptor (FXR), the peroxisome proliferator-activated receptor $\alpha$ (PPAR$\alpha$), and the receptor LXR$\alpha$ are members of a superfamily of approximately 150 proteins that bind to cis-acting elements in the promoters of their target genes and modulate gene expression in response to hormone activators or ligands. For many of these receptors, the activators are known, while for others, termed "orphan receptors," the activators are unknown. Furthermore, some of these receptors bind to their target genes as dimers consisting of two molecules of the same receptor (homodimers), while others bind as dimers consisting of one molecule each of two different receptors (heterodimers). Prominent among the latter are nuclear receptors that require heterodimerization with the retinoid X receptor, as disclosed by Yu, V. C., et al., "RXR$\beta$: a coregulator that enhances binding of retinoic acid, thyroid hormone, and vitamin D receptors to their cognate response elements," *Cell* 67:1251–1266 (1991). Members of this group include the vitamin D receptor, the thyroid hormone receptor ($T_3R$), the retinoic acid receptor (RAR), the farnesoid X-activated receptor (FXR), the peroxisome proliferator-activated receptors (PPAR), and LXR$\alpha$.

The farnesoid X-activated receptor (FXR) was first reported by Forman and coworkers, Forman, B. B., "Identification of a nuclear receptor that is activated by farnesol metabolites," *Cell* 81:687–693 (1995). This receptor is a protein having a relative molecular mass ($M_r$) of approximately 54,000, and is a vertebrate transcription factor regulated by intracellular metabolites. The receptor is activated by certain farnesoids, i.e., farnesol itself and compounds derived from, and/or similar in structure to, farnesol. These farnesoids include farnesol, farnesal, farnesyl acetate, farnesoic acid, geranylgeraniol, and juvenile hormone III. The chemical name for farnesol is 3,7,11,trimethyl-2,6,10-dodecatrienol, and the chemical name for juvenile hormone III is 7-methyl-9-(3,3-dimethyloxiranyl)-3-methyl-2,6-nonadienoic acid methyl ester. Farnesoids and metabolites that do not activate the FXR are geraniol, squalene, methoprene, mevalonate, squalene oxide, squalene dioxide, lanosterol, 24,25-epoxycholesterol, pregnenalone, dehydroepiandrosterone, bile acids, and 25-hydroxycholesterol. FXR activators of particular interest are farnesol (denoting trans,trans-farnesol hereinafter), farnesal, methyl farnesyl ether, ethyl farnesyl ether, methyl farnesoate, ethyl farnesoate, 7-methyl-9-(3,3-dimethyloxiranyl)-3-methyl-2,6-nonadienoic acid methyl ester, and 7-methyl-9-(3,3-dimethyloxiranyl)-3-methyl-2,6-nonadienoic acid ethyl ester. Preferred among these are farnesol, farnesal, methyl farnesyl ether, methyl farnesoate, and 7-methyl-9-(3,3-dimethyloxiranyl)-3-methyl-2,6-nonadienoic acid methyl ester. Particularly preferred are farnesol and 7-methyl-9-(3,3-dimethyloxiranyl)-3-methyl-2,6-nonadienoic acid methyl ester (juvenile hormone III).

Peroxisome proliferator-activated receptors (PPAR) are described in a review article by Schoonjans, K., "Role of the peroxisome proliferator-activated receptor (PPAR) in mediating the effects of fibrates and fatty acids on gene expression," *J. Lipid Res.* 37:907–925 (1996). Three subtypes of PPAR have been identified, and these are designated as $\alpha$, $\beta$ (or $\delta$), and $\gamma$. The $\alpha$ subtype has been cloned from Xenopus, humans, mouse and rat; the $\beta$(or $\delta$) subtype from Xenopus, humans and mouse; and the $\gamma$ subtype from Xenopus, humans and hamster. The PPARs have a modular structure consisting of six functional domains. The one domain that serves as the DNA-binding domain contains about 66 amino acids and is stabilized by two zinc atoms, each binding to four invariant cysteine residues. Included among the activators for PPAR$\alpha$ are fibrates, and fatty acids other than short-chain ($<C_{10}$) fatty acids, long-chain monounsaturated fatty acids, and dicarboxylic acids, particularly dodecanedioic acid. Also included are lower alkyl, preferably methyl, esters of the fibrates and lower alkyl, preferably methyl, esters of the fatty acids. Fibrates include:

clofibrate: 2-(4-chlorophenoxy)-2-methylpropanoic acid ethyl ester fenofibrate: 2-(4-(4-chlorobenzoyl)phenoxy)-2-methylpropanoic acid isopropyl ester ciprofibrate: 2-(4-(2,2-dichlorocyclopropyl)phenoxy) isobutyric acid gemfibrozil: 2-(2,4-dimethylphenoxypropyl)-2-methylpropanoic acid bezafibrate: 2-(4-(4-chlorobenzoylaminoethyl)phenoxy)-2-methylpropanoic acid Among the fatty acids, substituted fatty acids are particularly potent activators. PPARα activators of particular interest are linoleic acid, oleic acid, 5,8,11,14-eicosatetraynoic acid, (4-chloro-6-(2,3-xylidino)-2-pyrimidinyl)thioacetic acid, and clofibrate. A list including these and other examples of PPARα activators is as follows:

2,4-dichlorophenoxyacetic acid
2,4,5-trichlorophenoxyacetic acid
2-methyl-4-chlorophenoxyacetic acid
2-phenoxy-2-methylpropanoic acid ethyl ester
2-(4-bromophenoxy)-2-methylpropanoic acid ethyl ester
2-(4-iodophenoxy)-2-methylpropanoic acid ethyl ester
2-(2-chlorophenoxy)-2-methylpropanoic acid ethyl ester
2-(3-chlorophenoxy)-2--methylpropanoic acid ethyl ester
2-(4-chlorophenoxy)-2-methylpropanoic acid ethyl ester
2-(4-(4-chlorophenyl)phenoxy)-2-methylpropanoic acid ethyl ester
2-(4-(4-chlorobenzoyl)phenoxy)-2-methylpropanoic acid isopropyl ester
2-(4-(2,2-dichlorocyclopropyl)phenoxy)-2-methylpropanoic acid
2-(4-(4-chlorobenzoylaminoethyl)phenoxy)-2-methylpropanoic acid
2-(2,3-dimethyl-4-(1,2,3,4-tetrahydronaphth-1-yl)phenoxy)acetic acid
2-(2-methyl-3-ethyl-4-(4-chlorobenzyl)phenoxy)acetic acid
(4-chloro-6-(2,3-xylidino)-2-pyrimidinyl)thioacetic acid
2-((4-chloro-6-(2,3-xylidino)-2-pyrimidinyl)thioacetamido)ethanol
perfluoro-n-decanoic acid
di-(2-ethylhexyl)adipate
di-(2-ethylhexyl)phosphate
di-(2-ethylhexyl)sebacate
bis-(carboxymethylthio)-1,10-decane
ethyl 4-(4-chlorophenoxy)butanoate
2-(2-nitro-5-(2-chloro-4-trifluoromethylphenoxy)benzoyloxy)propanoic acid ethyl ester
2-(4-(4-chlorobenzoyl))phenoxy-2-(2-methylpropionamido)ethylsulfonic acid
tetradecyloxyacetic acid
tetradecyloxypropionic acid
perfluorobutanoic acid
perfluorooctanoic acid
tetradecylthioacetic acid
tetradecylthiopropionic acid
di-(2-ethylhexyl)phthalate
mono-(2-ethylhexyl)phthalate
2-ethylhexanoic acid
2-propylhexanoic acid The receptor LXRα was first described by Willy, P. J., et al., "LXR, a nuclear receptor that defines a distinct retinoid response pathway," *Genes & Development* 9:1033–1045 (Cold Spring Harbor Laboratory Press), and is named LXRα due to its initial isolation from the liver and its liver-rich expression pattern. The activators of LXRα are a subset of oxysterols, including 7α-hydroxycholesterol, 25-hydroxycholesterol, 27-hydroxycholesterol, 4β-hydroxycholesterol, 24-hydroxycholesterol, 20(S)-hydroxycholesterol, 22(R)-hydroxycholesterol, and 20,22-dihydroxycholesterol. Structurally similar compounds that are not activators of LXRα include cholesterol itself and the oxysterols 7,25-dihydroxycholesterol, 17α-hydroxycholesterol, and 22(S)-hydroxycholesterol (enantiomer of 22(R)-hydroxycholesterol). The numbering convention used for substituted cholesterols is as follows:

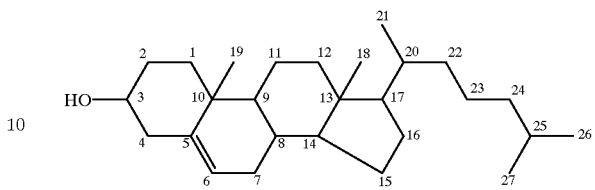

The term "activator" is used in this specification to denote any molecular species that results in activation of the indicated receptor, regardless of whether the species itself binds to the receptor or a metabolite of the species binds to the receptor when the species is administered topically. Thus, the activator can be a ligand of the receptor or it can be an activator that is metabolized to the ligand of the receptor, i.e., a metabolite that is formed in tissue and is the actual ligand.

The invention is useful in the treatment of acne *vulgaris* and acneiform skin conditions. Examples of acneiform skin conditions are:

acne conglombata;

hidradenitis suppurativa;

acne rosacea;

seborrhea;

seborrheic dermatitis;

gram negative folliculitis;

pyoderma faciale;

steatocystoma multiplex;

sebaceous hyperplasia; and rhinophyma.

In the practice of this invention, the activators will be administered as active ingredients in a formulation that is pharmaceutically acceptable for either topical, intralesional or systemic administration. These formulations may or may not contain a vehicle, although the use of a vehicle is preferred. Preferred vehicles, particularly for topical or intralesional administration, are non-lipid vehicles, particularly a water-miscible liquid or mixture of liquids. Examples are methanol, ethanol, isopropanol, ethylene glycol, propylene glycol, and butylene glycol, and mixtures of two or more of these compounds.

The concentration of active ingredient in the vehicle is not critical to this invention and may vary widely while still achieving a therapeutic effect, a preventive effect, or both. In most cases, concentrations within the range of from about 1 mM to about 50 mM, preferably from about 1 mM to about 20 mM, and most preferably from about 2 mM to about 10 mM, will give the best results. When using a formulation containing clofibrate, the preferred dosage is a twice-daily topical administration at a concentration of 10 mM; for juvenile hormone III, the preferred dosage is a twice-daily topical administration at a concentration of 2 mM; and for 25-hydroxycholesterol, the preferred dosage is a twice-daily topical administration at a concentration of 2 mM.

The invention is generally applicable to the treatment of the skin of terrestrial mammals, including for example humans, domestic pets, and livestock and other farm animals. The invention is of particular interest in treating humans for the conditions described above or for preventing these conditions from becoming manifest.

The following examples are offered for purposes of illustration, and are not intended to limit nor to define the invention. All literature citations in these examples and throughout this specification are incorporated herein by reference for all legal purposes to be served thereby. The compounds used in these examples were as follows:

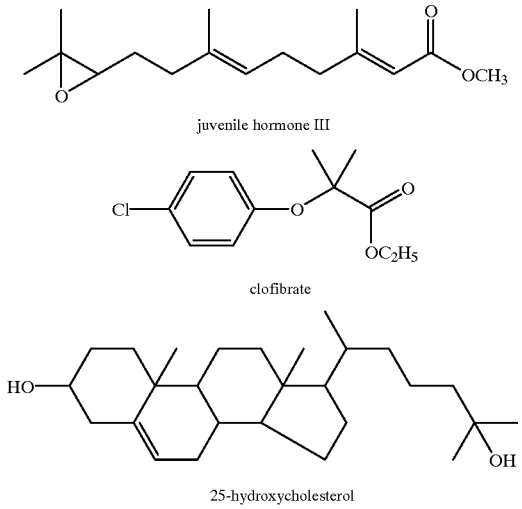

juvenile hormone III clofibrate 25-hydroxycholesterol

EXAMPLE 1

This example illustrates the effects of the activators of this invention on sebaceous glands when the activators are topically applied to normal adult murine skin.

A representative member of each of the three classes of activators was used: FXR activators were represented by farnesol, PPARα activators were represented by clofibrate, and LXRα activators were represented by 22(R)-hydroxycholesterol. Normal adult hairless mice, 6–8 weeks old, were topically treated with each of the three representative activators, by dissolving the agents in propylene glycol/ethanol (7:3 on volume basis) at a concentration of 0.5–10 mM, and applying 0.4 cc to 6 $cm^2$ areas on the flanks of the mice, twice daily for 4.5 days (9 treatments total). As controls, treatments were made of the vehicle alone to opposing flanks on the same animals and to flanks on separate animals to which test compounds were not applied.

After five days, samples of the flanks were taken and the following observations were made:

(a) The volume of the sebaceous glands was observed before and after treatment, which indicated that the volume had noticeably decreased due to the treatment.

(b) The number of mitotic figures in the sebaceous gland epithelium was noted both before and after treatment, and had decreased by 30–50% due to the treatment.

(c) Fluorescent staining to detect lipids was performed with oil red O and neutral red, both before and after treatment, with the result that the intensity of the staining was noticeably reduced as a result of the treatment.

These results suggested that involution of the sebaceous glands had occurred.

EXAMPLE 2

This example utilizes an accepted model for screening compounds for acne therapy—the flank organs of male Syrian hamsters, which organs contain unusually large sebaceous glands. The test compounds were juvenile hormone III to represent FXR activators, clofibrate to represent PPARα activators, and 25-hydroxycholesterol to represent LXRα activators.

Before applying the test compounds, the flanks and backs of Syrian golden hamster males were shaved, and full-thickness skin biopsies were taken from both flanks. Immediately after the biopsies were taken, one flank of each animal was treated with a treatment solution of one of the test compounds dissolved in ethanol. The concentration of each treatment solution is given in the table below, and the amount applied was 0.4 mL to a flank surface area of 6 $cm^2$. Repeat treatments of the same solutions (in the same amounts) to the same flanks were administered eight hours after the first treatment. Simultaneously with each treatment, the opposite flank of each animal was treated in an identical manner but with ethanol alone. A further group of animals was treated with ethanol alone on one flank (simultaneously and in a manner identical to the treatments of the other groups), while the opposite flank was left untreated.

Five days after the treatment, biopsies were again taken over both the treated and control sites. All samples were fixed in 4% paraformaldehyde, embedded in paraffin, and sectioned (5 $\mu m$). The flank organ volume was determined by taking micrographs of the sections and using a planimeter around the sebaceous glands in a 100 $\mu m^2$ field in five randomly selected sections of each micrograph. The results are shown in Table I below.

TABLE I

Hamster Flank Assay: Effect of Test Compounds on Flank Organ Volume

| Test Compound (concentration; number of animals in group) | Pre-Treatment | Sig-nificance | Post-Treatment (5 days) |
|---|---|---|---|
| | Mean Cross Sectional Area ($\mu m^2$ of sebaceous gland per 100 $\mu m^2$ field ± SEM) | | |
| Clofibrate (10 mM; n = 4) | 87 ± 7.5 | p < 0.005 | 56 ± 4.0 |
| Juvenile Hormone III (2 mM; n = 5) | 89 ± 6.0 | p < 0.05 | 71 ± 5.2 |
| 25-Hydroxycholesterol (2 mM; n = 5) | 89 ± 9.2 | p < 0.01 | 62 ± 5.3 |
| Vehicle Alone (n = 4) | 85 ± 8.3 | not significant | 86 ± 8.0 |

The consistent reductions in the volume of the flank organ that result from treatment with each of the test compounds indicates that the compounds will be useful as therapeutic agents for the treatment of acne.

EXAMPLE 3

This example illustrates another standard acne assay for anti-acne activity, which involves a determination of whether the test compounds prevent the development of hydrocarbon-induced comedones on the ventral surface of rabbit ears. The test compounds were juvenile hormone III to represent the FXR activators, clofibrate to represent the PPARα activators, and 25-hydroxycholesterol to represent the LXRα activators.

The tests were performed on male New Zealand rabbits, with two rabbits in each group. Each rabbit was treated on a 2.5 $cm^2$ diameter circular area of the ventral surface of one ear with 1 cc of the test compound dissolved in hexadecane (at various concentrations as listed in Table 11 below), and on the ventral surface of the other ear with hexadecane alone. Treatments were administered twice daily for twelve days. The number of comedones that appeared after the treatment period were counted, and the number at the sites treated with both the test compound and the hexadecane vehicle were compared with those at the sites treated with the vehicle alone. The results are shown in Table II below.

TABLE II

Rabbit Ear Assay: Effect of Test Compounds on Comedone Formation

| Test Compound (number in sample) | Concentration Applied | Percent Reduction | Significance (vs. Vehicle) |
|---|---|---|---|
| Clofibrate | 10 mM | 62 ± 7.0 | $p < 0.001$ |
| (n = 4) | 5 mM | 37 ± 3.0 | $p < 0.05$ |
|  | 1 mM | 5 ± 1.5 | not significant |
| Juvenile Hormone III | 2 mM | 35 ± 4.0 | $p < 0.05$ |
| (n = 4) | 1 mM | 18 ± 2.0 | $p < 0.1$ |
|  | 0.5 mM | 7 ± 1.5 | not significant |
| 25-Hydroxycholesterol | 2 mM | 73 ± 8.5 | $p < 0.001$ |
| (n = 4) | 1 mM | 38 ± 6.2 | $p < 0.05$ |
|  | 0.5 mM | 21 ± 3.8 | $p < 0.1$ |
| Vehicle (n = 4) | — | 0 | — |

The consistent reductions in the number of comedones at concentrations above 1 mM indicate that the test compounds are useful as therapeutic agents for the treatment of acne.

The foregoing is offered primarily for purposes of illustration. It will be readily apparent to those skilled in the art that the concentrations, operating conditions, materials, procedural steps and other parameters of protocols described herein may be further modified or substituted in various ways without departing from the spirit and scope of the invention.

We claim:

1. A method for treating a terrestrial mammalian subject suffering from a condition selected from acne and acneiform conditions, said method comprising administering to said subject a composition containing 7-methyl-9-(3,3-dimethyloxiranyl)-3-methyl-2,6-nonadienoic acid methyl ester in a concentration that is effective in reducing the degree of said condition.

2. A method in accordance with claim 1 in which said concentration is from about 1 mM to about 50 mM.

3. A method in accordance with claim 1 in which said concentration is from about 2 mM to about 10 mM.

* * * * *